(12) United States Patent
Garton et al.

(10) Patent No.: US 7,875,254 B2
(45) Date of Patent: *Jan. 25, 2011

(54) INTERNAL LOOP REACTOR AND OXO PROCESS USING SAME

(75) Inventors: Ronald Dean Garton, Baton Rouge, LA (US); Matthew Findlay, Hythe (GB); Krishnan Sankaranarayanan, South Riding, VA (US); Arie Van Vliet, Sterrebeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/652,171

(22) Filed: Jan. 5, 2010

(65) Prior Publication Data

US 2010/0105956 A1   Apr. 29, 2010

Related U.S. Application Data (63) Continuation of application No. 11/484,178, filed on Jul. 10, 2006, now Pat. No. 7,666,366.

(51) Int. Cl.
B01J 19/18 (2006.01)
F28D 7/00 (2006.01)

(52) U.S. Cl. ............... 422/227; 422/211; 422/200; 518/726; 568/451

(58) Field of Classification Search ............ 422/200, 422/211, 227; 518/726; 568/451
See application file for complete search history.

(56) References Cited

U.S. PATENT DOCUMENTS

| 3,431,188 | A | 3/1969 | Ito et al. |
|---|---|---|---|
| 4,312,837 | A | 1/1982 | Papp et al. |
| 4,342,876 | A | 8/1982 | Klingman |
| 5,277,878 | A | 1/1994 | Piotrowski et al. |
| 5,503,810 | A | 4/1996 | Chang |
| 5,763,678 | A | 6/1998 | Beckers et al. |
| 5,955,041 | A | 9/1999 | Arnold et al. |
| 5,961,933 | A | 10/1999 | Casanave et al. |
| 6,106,789 | A | 8/2000 | Thompson et al. |
| 6,162,754 | A | 12/2000 | Maretto et al. |
| 6,162,757 | A | 12/2000 | Chang et al. |
| 6,544,421 | B2 | 4/2003 | Haridas et al. |
| 2005/0080147 | A1 | 4/2005 | Hawthorne et al. |

(Continued)

FOREIGN PATENT DOCUMENTS

FR   1 512 557   9/1968

(Continued)

OTHER PUBLICATIONS

J. Falbe, Ed., "New Syntheses with Carbon Monoxide," Spring-Verlag, New York (1980), pp. 16-17.

Primary Examiner—Walter D Griffin
Assistant Examiner—Natasha Young
(74) Attorney, Agent, or Firm—Andrew B. Griffs; Leandro Arechederra (57) ABSTRACT

The invention relates to improvements in internal loop reactors. The reactor of the invention is characterized by a plurality of cooling tubes which form the annulus between the riser and the downcomer path of said internal loop reactor. The reactor also provides improvements in hydroformylation reactions using the improved reactor.

14 Claims, 5 Drawing Sheets

U.S. PATENT DOCUMENTS

2006/0041166 A1* 2/2006 Stuart .................. 560/348
2008/0009554 A1   1/2008 Garton et al.

FOREIGN PATENT DOCUMENTS

| JP | 10339524 A * | 12/1999 |
| WO | WO 88/04317 | 6/1988 |
| WO | WO 00/35852 A1 * | 6/2000 |
| WO | WO 2005/058782 A1 * | 6/2005 |
| WO | WO 2007/086610 | 8/2007 |
| WO | WO 2008/051301 A2 * | 5/2008 |

* cited by examiner

INTERNAL LOOP REACTOR AND OXO PROCESS USING SAME

CROSS REFERENCE TO RELATED APPLICATION

This application is a continuation of Ser. No. 11/484,178, filed Jul. 10, 2006, now U.S. Pat. No. 7,666,366, the disclosure of which is herein incorporated by reference in its entirety.

FIELD OF THE INVENTION

The invention relates to improvements in reactors, particularly internal loop reactors. In embodiments, there are also improvements in heterogeneous (gas/liquid phase) exothermic reactions, particularly hydroformylation reactions, using the improved reactor.

BACKGROUND OF THE INVENTION

The hydroformylation reaction, also known as the Oxo Reaction or Oxo Process, consists in reacting a synthesis gas made up of a mixture of carbon monoxide and hydrogen and at least one $C_nH_{2n}$ olefin so as to obtain a mixture of aldehydes and primary alcohols containing n+1 carbon atoms. The reaction is generally catalyzed with carbonyls of transition metals such as cobalt. This type of reaction is described in detail in patents too numerous to recite. It is commercially highly important, producing products that find uses in plastics, soaps, lubricants, and other products.

The reactors in which the Oxo Process is carried out can be identical or different in all process stages. Examples of types of reactor which can be used are bubble columns, loop reactors, jet nozzle reactors, stirred reactors and tube reactors, some of which can be cascaded and/or provided with internals.

As part of the reactor of the "loop" type the liquid phase is recycled and the gas phase is allowed to exit the reactor at the top of the loop. External loop reactors are illustrated, for instance, in U.S. Pat. No. 4,312,837 (Papp et al.). The typical reactor used in Oxo is an external loop reactor, but internal loop reactors are also used.

Figure 1:
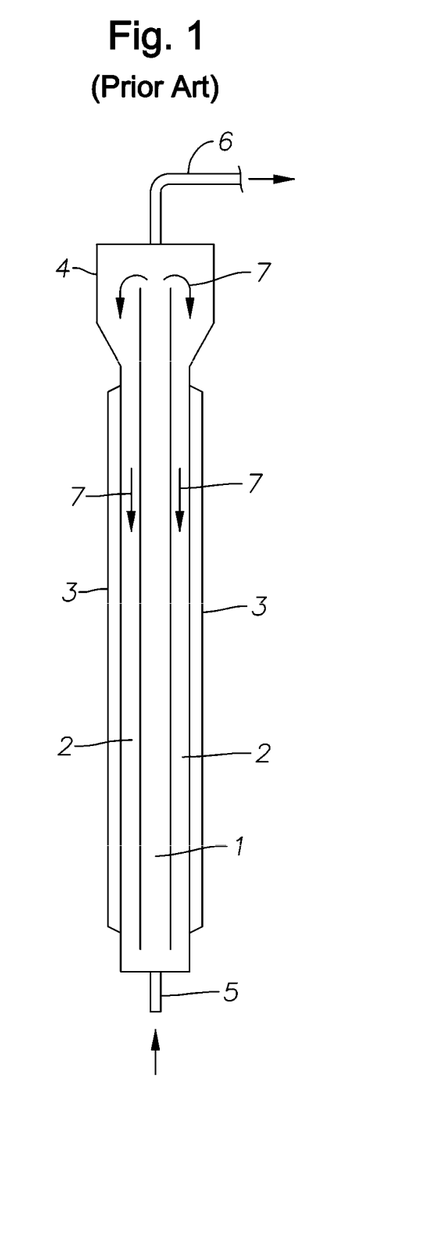
FIG. 1 shows the side view of a prior art internal loop reactor.

An example of an conventional internal loop reactor is illustrated in FIG. 1 of the present disclosure. Such a reactor is made up of at least two concentric vertical tubes 1 and 2 connected to each other at their upper and lower ends. As shown in FIG. 1, the vertical column 1 of loop reactor 4 acts as the ascending branch ("riser") while vertical column 2 acts as the descending branch ("downcomer"). The vertical columns are supplied with jacketed cooling means 3. Ascending vertical column 1 is continuously supplied at its base with the synthesis gas and liquid phase through inlet 5. Essentially all the synthesis gas and the excess liquid phase is evacuated at the upper connection 6, while essentially only the liquid phase circulates between ascending column 1 and descending column 2, said circulation illustrated by arrows 7. The difference between the specific gravities of the gas/liquid phase mixture on the one hand and the liquid phase alone on the other hand results in a difference in hydrostatic pressure between the ascending branch and the descending branch, thus leading to circulation of the liquid phase in the reactor.

Loop reactors of both the internal and external type are used in reactions other than the Oxo Process. They are useful particularly in exothermic and/or heterogenous (gas/liquid) reactions and have been used for such diverse reactions as the oxidation of p-xylene (U.S. Pat. No. 4,342,876), biotechnological reactions (WO 8804317), and the purification of water (U.S. Pat. No. 6,544,421). It is known that by varying the geometries of the reactor, it is possible to eliminate certain problems encountered in specific reactions. See, for instance, U.S. Pat. No. 4,312,837 (FR 2430794 A1); U.S. Pat. Nos. 4,342,876; 5,277,878; 5,503,810; and 6,106,789. There is, however, no shortage of problems to be solved in these systems and typically solving one problem by simply varying geometries introduces at least one new problem.

One of the main problems with conventional loop reactors, is that they are limited in size. At least in part this is simply a matter of the practical difficulty in bending large tubes. In addition, construction of large reactors is also made difficult because the vessels must be erected in the field by sliding internals, which must be standing vertically; otherwise, with reactor on its side, the internals will bend and warp. Furthermore, in the case of the Oxo Process, the reaction typically occurs at very high pressures, such as 4,000 lbs/in (or about 28 MPa), which further limits the size of the vessels as they are known to be constructed in the prior art. As far as the present inventors are aware, the largest known loop reactors have a volume of about 8-12 cubic meters.

The present inventors have discovered that by building an internal loop reactor so that the separation between the riser and downcomer portions comprises a heat exchanger, preferably one or more cooling tubes, allows for all the necessary parts to be attached to a reactor head. This allows more convenient construction of the reactor in the field and furthermore reactor volume can be increased considerably over prior art Oxo Reactors.

SUMMARY OF THE INVENTION

The invention is directed to an internal loop reactor having a heat exchanger defining barrier between riser and downcomer sections, said barrier referred to herein as the draft tube. The draft tube, which in an embodiment comprises one or more cooling tubes, is preferably in an elongated annular or cylindrical shape, but may take some pattern other than circular pattern, e.g., a polygon pattern, or a multipointed star pattern, or an irregular pattern.

In an embodiment, the single cooling tube (or cooling annulus) or plurality of cooling tubes forming the draft tube are attached to the top of the reactor so as to allow circulation of the liquid phase to the outside downcomer part of the internal loop reactor. In addition, the connection of virtually all necessary internal parts to the top of the reactor allows for ease of construction, as will become apparent in the following disclosure.

In another embodiment, the plurality of cooling tubes are attached to each other by "webs" or metal strips attached, such as by welding, between the tubes over a predetermined length, such as determined to be the optimum for the height and position of the riser.

In a preferred embodiment the bottom portion of the reaction vessel has a hemispherical bottom.

In yet another embodiment, lateral support for the single cooling tube or plurality of cooling tubes is provided by at least one lateral support rod so as to connect one or more cooling tubes or webs to the outer vessel wall. In preferred embodiment the one or more lateral support rods are hinged at the vessel wall and/or at the connecting point of the one or more cooling tubes or webs. In another preferred embodiment the one or more lateral support rods are constructed of a material that allows flexibility, such as bending.

In still another embodiment, a cooling jacket is attached to the reactor shell to provide heat transfer from the reactor.

In yet still another embodiment, there is a method of constructing a large scale internal loop reactor wherein all necessary internal parts are connected to a reactor head which can be lowered into a fixed, vertical shell reactor vessel to facilitate construction and maintenance in the field.

The invention is also directed to a chemical reaction, more preferably an exothermic and/or heterogenous (gas/liquid phases) reaction, and still more preferably the Oxo Process, carried out in the reactor according to the invention.

It is an object of the invention to facilitate ease of construction and maintenance in the field and allow process scale-up for reactions in reactors of the loop-type.

These and other objects, features, and advantages will become apparent as reference is made to the following drawings, detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

According to the invention, an internal loop reactor is characterized by a heat exchanger, preferably comprising at least one cooling tube, and more preferably a plurality of cooling tubes, forming the barrier between the riser and the downcomer path of said internal loop reactor, said barrier forming what it referred to herein as the draft tube.

Figure 2A:
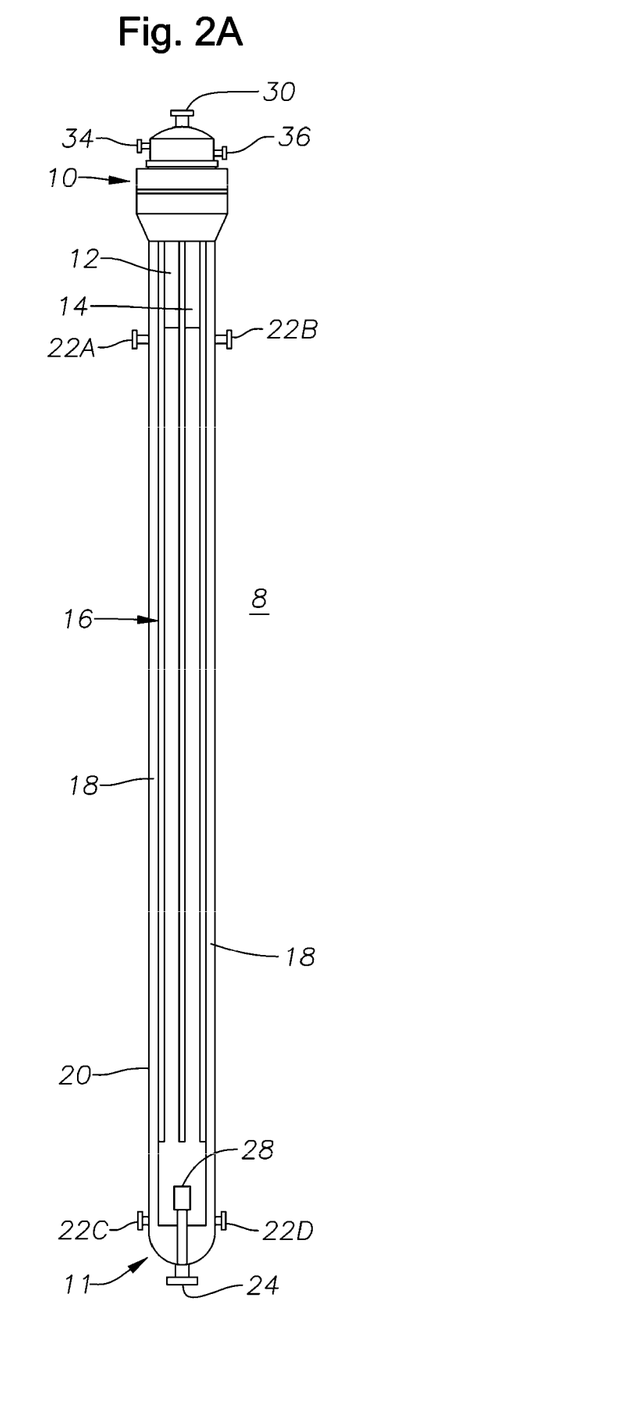
FIG. 2A illustrates a side view of a reactor according to an embodiment of the present invention and FIG. 2B illustrates certain detailed features of such a reactor.

As shown in a side view of an embodiment of the reactor according to the invention provided by FIG. 2A, the internal loop reactor 8 comprises a pressure vessel 20 containing a cylinder or draft tube 16 suspended from vessel head 10 along the vessel centerline. The draft tube 16 is formed by the cooling tubes with optional connecting web or sheets and provides, inside of draft tube 16, the riser column (which is equivalent in function to riser column 1 in FIG. 1). In a preferred embodiment, a two-phase mixture comprising syngas and Oxo product and/or reactants from the upstream reactors is fed to the bottom of the reactor through inlet 24 and directed, such as by optional sparger 28, into the internal riser column provided by draft tube 16. At the top of the riser, gas partially or wholly disengages from the riser outlet and exits the reactor at the top through outlet 30. Liquid, which is at least now partially, virtually, or completely free of gas, flows through gaps or windows 12 and 14 in the upper portion of draft tube 16, and falls down the annular space 18 (downcomer column) between draft tube 16 outer wall and the inner wall of vessel 20, enters the riser column inside of draft tube 16 at the bottom of draft tube 16 (see also arrow 700 in FIG. 2B indicating flow direction) to mix with the fresh feed provided through inlet 24, setting up an internal circulation loop. (In the preferred embodiment wherein the reaction is the Oxo Reaction, it is preferred that at least some gas goes over into the downcomer so that the reaction continues to some extent in downcomer column 18. By way of non-limiting example, if the riser column contains 10% by volume gas, it may be convenient to have the downcomer column contain 3% by volume gas in the upper portion of the downcomer. This may be achieved by proper dimensions of the reactor and/or reaction variables such as concentration of ingredients, temperature, etc.). The pressure vessel 20 is preferably fitted with a hemispherical bottom 11. Conveniently, the hemispherical bottom may be removeably affixed or hinged to facilitate inspection and maintenance of the reactor. Features 34 and 36 in FIG. 2 relate to the cooling medium provided to the plurality of cooling tubes and are explained in detail with reference to FIG. 3, below. Features 22A, 22B, 22C, and 22D are optional thermocouples or other devices which may be used to monitor and/or control, such as by an operator and/or with the aid of a computer, the temperature of the reaction/reactor.

One of the advantages of the present invention is that the scale of the Oxo Reaction can be greatly increased from conventional loop reactors used in said Reaction. In preferred embodiments, the reactor 8 may have, by way of example and not to be construed as limiting, an internal volume on the order of 20-40 cubic meters operating with a recirculation rate of 700-900 cubic meters per hour and velocities in the riser and downcomer of about 0.4-0.6 meters/second. In embodiments, the internal diameter of vessel 20 can be on the order of 1 to 2 meters, and the height of the vessel 20 (extending up to the head 34) on the order of 20-30 meters. The ratio of the area of the downcomer portion to riser portion is preferably close to unity and can conveniently range from 0.5 to 1.5. However, these numbers may be varied depending on the reaction and desired results and should not be taken at critical limitations. Without wishing to be bound by theory, in embodiments, such a reactor is essentially a nearly isothermal, continuous stirred tank reactor (CSTR).

The materials with which to construct the apparatus of the invention do not form a part of the present invention and the various parts may be constructed of conventional materials, e.g., the vessel sidewall 20 in FIG. 2A may be solid alloy, carbon steel with a bonded liner, and the like.

An essential feature of the present invention is that temperature control of the reactor is provided by the heat exchanger (e.g., cooling tube(s)) which also form an essential geometric feature of the internal loop, i.e., the riser and downcomer columns separated by the draft tube comprising said heat exchanger. Typically the riser and downcomer columns will be concentric tubes, which implies that, viewed from the top, the columns comprise essentially two concentric circles, but the shapes do not have to be circular, as will become apparent in this detailed description. Additional temperature control may be provided by optional cooling jacket provided against the vessel wall (not shown in FIG. 2A) as in conventional reactors, e.g., analogous to element 3 in FIG. 1.

In preferred embodiments the surface area of the heat exchanger (e.g., one or more cooling tubes) forming the draft tube is made large enough such that the reactor temperature is open loop stable such that no feedback control is needed on the reactor temperature itself. The recirculating cooling water (or heating water, as the case may be) temperature is the only required control system. It will be appreciated by ordinary artisan that the heat exchange medium may be some other fluid besides water, e.g., a hydrocarbon fluid.

Figure 2B:
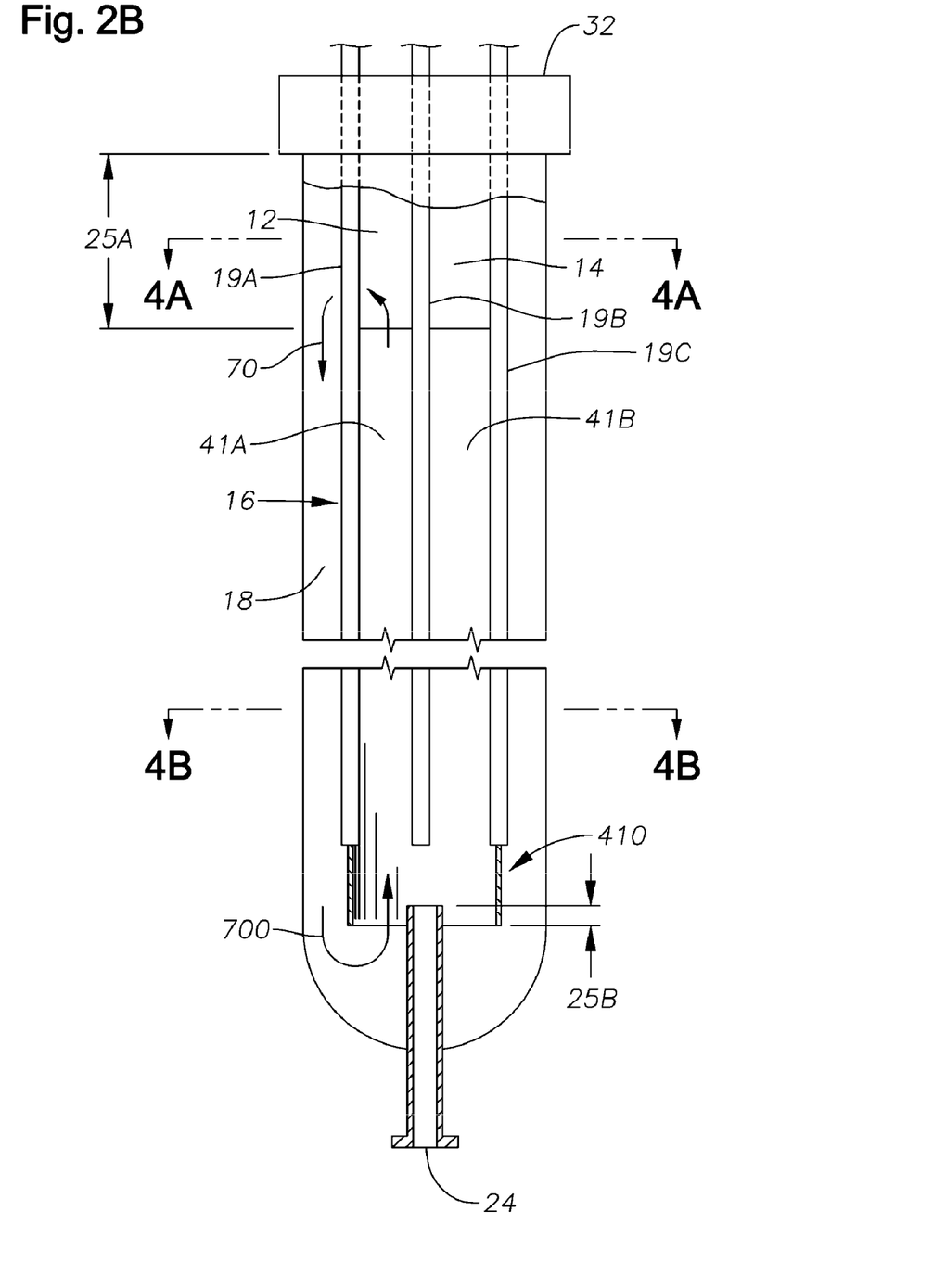

FIG. 2B illustrates some details not shown in FIG. 2A. In FIG. 2B, there are plural cooling tubes 19A, 19B, 19C etc., which together with plate or webs 41A, 41B, etc., form draft tube 16. Plates or webs 41A, 41B, etc., does not extend all the way to plate or tubesheet 32 (discussed in more detail with respect to FIG. 3) but rather at least a portion of the plate or web 41 is omitted so as to provide at least one window or gap(s) 12, 14, etc., whereby the liquid, at least partially free of gas, flows into the downcomer 18, as illustrated by arrow 70. As shown in FIG. 2B, the gap(s) 12, 14, etc., are spaced a distance 25A from element 32, with distance 25A being readily determined by one of ordinary skill in the art in possession of the present disclosure. When there are plural gaps, as shown in this embodiment (12 and 14) the gap distance 25A does not need to be the same for each gap. In the embodiment illustrated in FIG. 2B, the plates or webs 41A, 41B, etc., may be extended below the bottom of the cooling tubes 19A, 19B, 19C, etc., shown by element 410, to at least partially enclose the top of the inlet provided by element 24, discussed above with respect to FIG. 2A. However, this extension of the connective web or sheet is merely optional, and in a preferred embodiment the cooling tubes 19A, 19B, 19C, etc., as well as the connect webs or sheets 41A, 41B, etc., extend below the top of inlet 24, so that the feed entering through inlet 24 enters the loop reactor inside the draft tube 16). Thus draft tube 16, which in the center portion comprises heat exchanger(s) such as 19A, 19B, 19C, etc., and optional plates or webs 41A, 41B, etc., may comprise only the plate or web 410 in the lower portion. The distance by which the cooling tube(s) 19A, 19B, 19C, extend beyond the plates or webs 41A, 41B, etc., (if at all), or in the embodiment illustrated, the distance by which the plate or web 410, extends beyond the cooling tube(s), (if at all), and likewise the distance 25B by which the inlet tube (with optional sparger) extends up into the draft tube (if at all) may be predetermined by one of ordinary skill in the art. Thus, in an embodiment the plates or webs 41A, 41B, etc., may stop some distance prior to the bottom or the cooling tube(s) 19A, 19B, etc. Arrow 700 illustrates the movement of the liquid from the downcomer around the base of the draft tube 16 formed by plate or web 410 where the liquid is mixed with the material added through inlet 24 in the riser portion formed by draft tube 16.

Figure 4A:
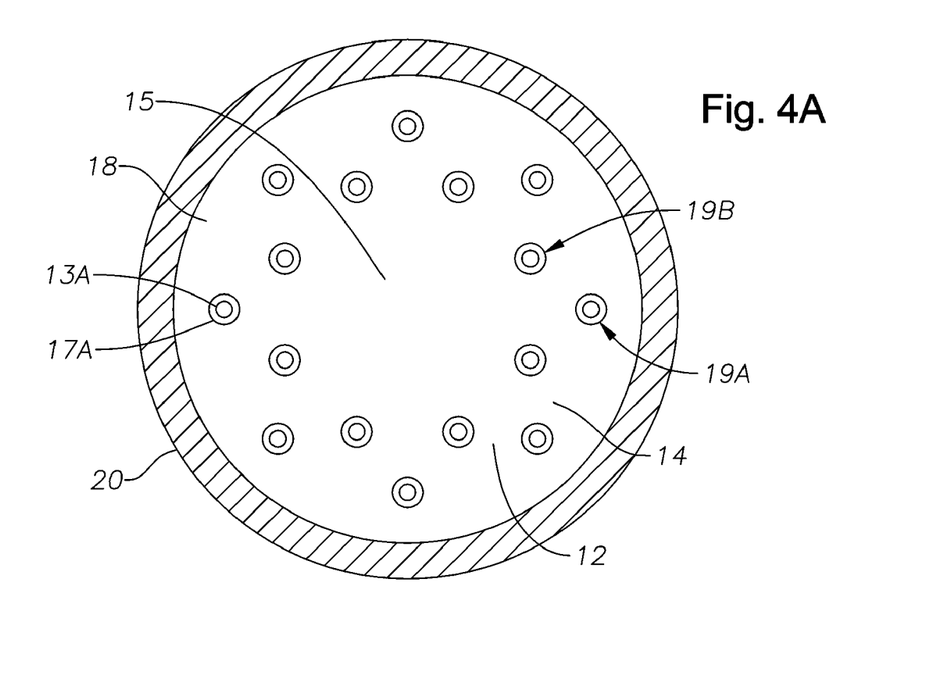
FIGS. 4A and 4B shows a top view and bottom view, respectively, of the arrangement of cooling tubes according to an embodiment of the invention.

In a preferred embodiment (not visible in FIG. 2B), in the upper portion of draft tube 16, in order to increase flow from the inside riser column 15 over to downcomer column 18, the draft tubes may be "dog-legged" in or out in an alternating fashion. For instance, in FIG. 2B, cooling tube 19B may be dog-legged inwardly (with respect to the centerline of the draft tube 16) while cooling tubes 19A and 19C may be dog-legged outwardly. More details of this preferred embodiment will become evident when FIG. 4A is discussed below.

Figure 3:
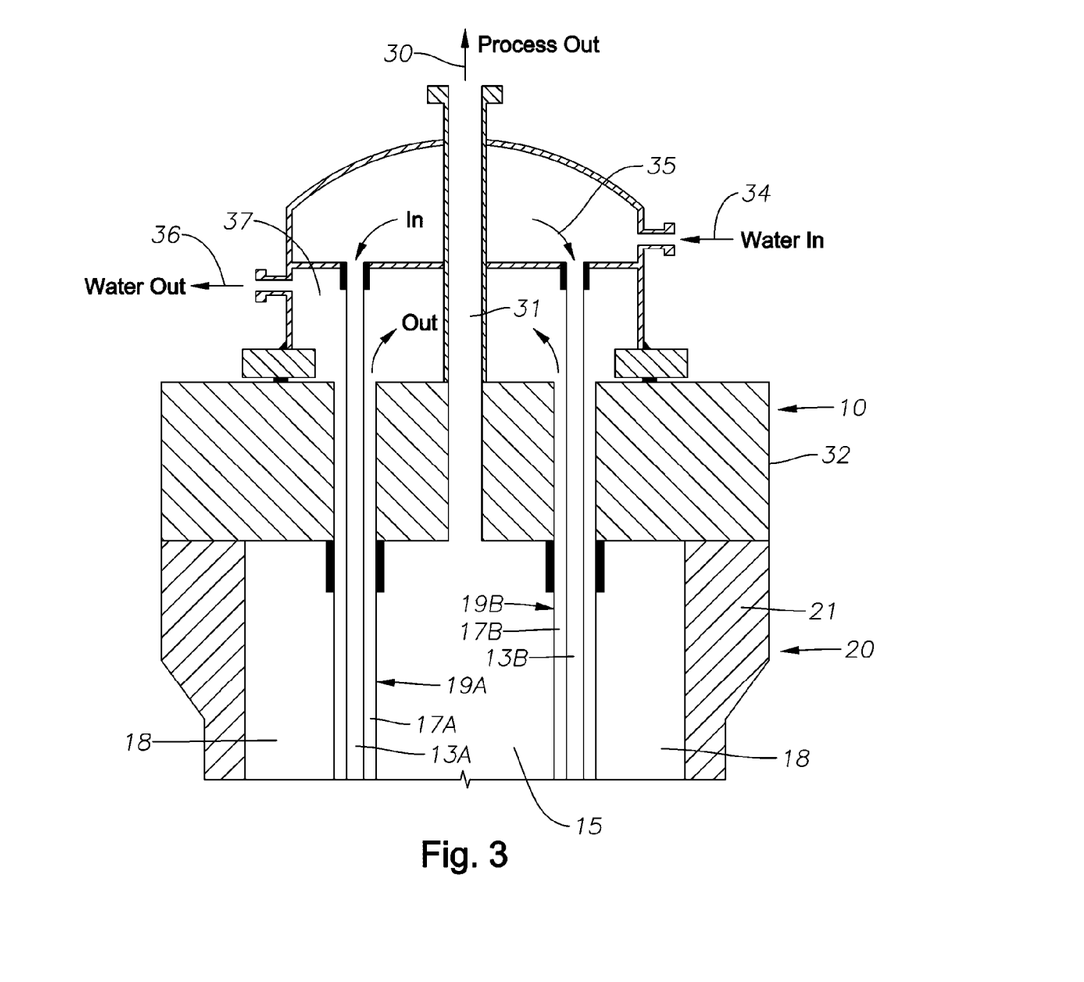
FIG. 3 provide a side view showing certain details of embodiments of the present invention as it relates to the top portion of the reactor.

FIG. 3 illustrates some of the details of an embodiment of the cooling system for the reactor of the invention. The head of the reactor, 10, contains part of the circulation system (or recirculation system) for the cooling medium, which may be provided by various liquids or gases as would be recognized by one of ordinary skill in the art but for convenience is typically water. In an embodiment, the top head will have two juxtaposed and interconnected compartments 35 and 37, respectively, the former from which the inlet 34 cooling water is distributed to the cooling tube or plurality of cooling tubes, and the latter to collect the return water which exits through outlet 36. The plural cooling tubes (shown by reference to two cooling tubes 19A, 19B, for the sake of clarity) may be arrayed as concentric bayonets-type tubes with the inlet water going down the center tubes 13A, 13B, and the outlet water coming up the outer concentric tube 17A, 17B, or vice versa. Although only two cooling tubes are shown in FIG. 3 for convenience of view, plural cooling tubes may be arranged concentrically (or in some other geometric pattern or irregular pattern) inside vessel wall 21 of vessel 20 so as to form downcomer space 18 and riser column 15. Riser space 15 allows the gas and excess liquid to exit out the reactor through conduit 31 in reactor head 10 to outlet 30. A single opening (i.e., here the top of the riser column 15) near the top of the plurality of cooling tubes (e.g., corresponding to window 12 in FIG. 2A and FIG. 2B) which allows circulation of the essentially gas-free or gas-depleted liquid down the downcomer; connective webs or sheets 41A, 41B, are not shown in FIG. 3. The various parts of reactor head 10 may be welded, adhesively connected, bolted, and the like (or combination thereof). Various alternative or auxiliary means of connections would be known to one of ordinary skill and may include the use of gaskets and the like.

The inner tube 13A passes through the outlet water compartment 36 and is open to the top water compartment 35. The outer tube 17A may be welded to the top head and is open to the outlet water compartment 36.

One of the unique advantages of the reactor system according to the present invention is that entire top head 10 comprising element 32 and internal assembly comprising a plurality of cooling tubes illustrated by tubes 19A, 19B, etc., can be lowered into the vertical shell during construction as well as lifted out of the shell for any serious maintenance.

Figure 4B:
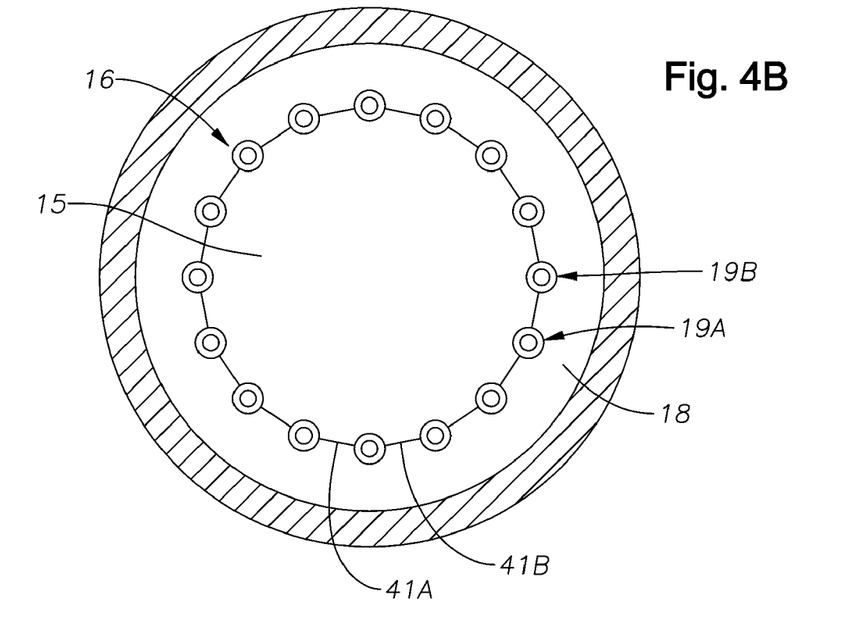

FIG. 4 illustrates an embodiment of the draft tube (16 in FIGS. 2A and 2B) wherein the draft tube comprises plural cooling tubes formed by cooling tubes 19A, 19B, etc. FIG. 4A is a view taken of a preferred embodiment from the top portion of vessel 20 showing only the position of the "dog-legged" tubes (above the connecting sheet or web 41A, 41B, etc. in FIG. 2B). In contrast, FIG. 4B is a view taken from the middle portion of the vessel 20 with the hemispherical end cap (11 in FIG. 2) removed, and shows the connective sheet or webs 41A, 41B, etc. between each cooling tube.

In the arrangement shown in FIG. 4, the schematic view is best understood first by reference to FIG. 4B. It will be understood that the array of plural cooling tubes 19A, 19B, etc., can be in some other geometric arrangement than that shown, such as in a square configuration, and the like. Cooling tubes 19A, 19B, etc. may be welded together or connected such as by sheet metal as shown by elements 41A, 41B, etc., so that the combination of plural cooling tubes and connective webs or sheets form the draft tube 16. The connective sheets or webs 41A, 41B, etc., connect the plural cooling tubes from near the bottom portion of the draft tube to near the upper portion of the draft tube, the exact distance from the top and bottom being predetermined. The selection of distance between top and bottom is preferably independently determined. The determination may be made by experiment or with the aid of computational fluid dynamic models using commercially available software, or a combination thereof. Using the reactor dimensions provided elsewhere in the present disclosure (i.e., with respect to vessel volume, height, diameter, etc.), it is sufficient but not required that the distance of the top of the draft tube from the top of the vessel and the distance of the bottom of the draft tube from the bottom of the vessel be on the order of 1 to 3 meters, with about 2 meters being preferred. Thus connected by the sheets or webs between each cooling tube, plural cooling tubes 19A, 19B, etc. form the draft tube that separates riser column 15 downcomer column 18.

As mentioned the plural connecting elements, illustrated by sheets or webs 41A and 41B in FIG. 4B, connect the plural cooling tubes 19A, 19B, etc., to a predetermined distance from the head of the reactor (32 in FIGS. 2B and 3) where the connecting web or sheet stops at said predetermined distance to provide at least one gap for recirculation. These gaps (12 and 14 in FIG. 2A and FIG. 2B) may be accentuated by altering the geometry of the cooling tubes near the top, such as illustrated in FIG. 4A, where the cooling tubes each take an alternating inward/outward "dog leg" to provide plural gaps, as discussed briefly above, thus providing or accentuating the gap between the individual cooling tubes 19A, 19B, etc., and fluid communication between riser column 15 and downcomer column 18. Thus, cooling tube 19A is dog-legged outwardly with respect to the center line of the cooling tube (not labeled in FIG. 4A) separating riser column 15 and downcomer column 18, while cooling tube 19B is dog-legged inwardly, and so on. The location of the bends for the dog legs is a convenience place to discontinue the connective plates or webs 41A, 41B, etc.

In consideration of the increased volume allowed in the reactor according to the invention, the exposure of bottom of the plural array of cooling tubes to the process pressures a significant buckling stress not encountered in the design of the existing internal loop reactors. This may be addressed in various ways such as by the embodiment illustrated in FIG. 5.

Figure 5:
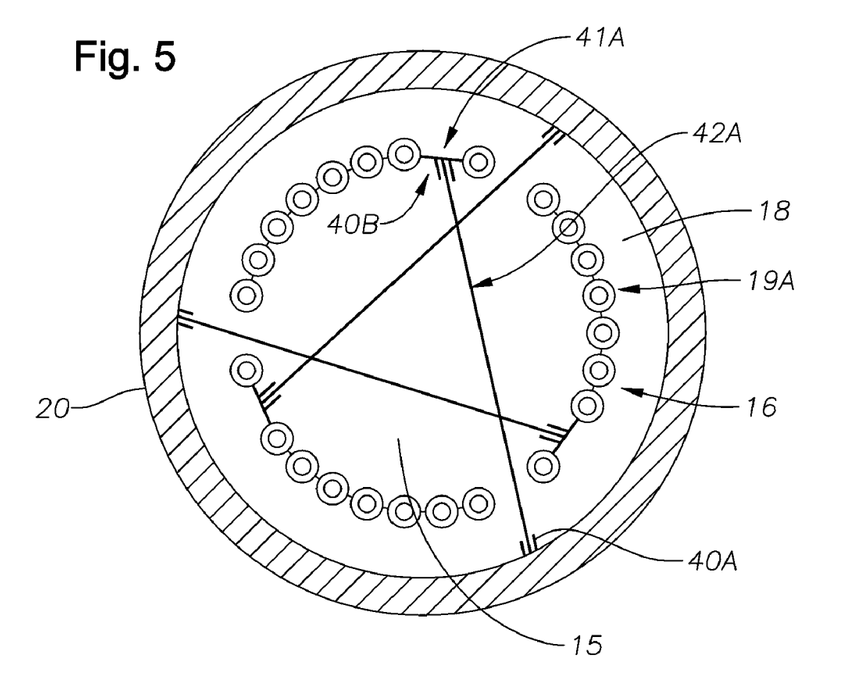
FIG. 5 illustrates the lateral support bars for the cooling tubes according to an embodiment of the invention.

In FIG. 5, the plural cooling tubes 19A, 19B, etc., are connected by plural webs or sheets, as discussed previously. In an embodiment, near the bottom of the draft tube, one or more of the tubes are cut short to allow the rod to pass through the draft tube. The other space on the other side has a wider sheet web to connect the rod to, as shown by connective sheet or web 41A. Element 42A is intended to provide support for the draft tube 16 (FIG. 2) comprising plural cooling tubes 19A, 19B, etc. against the stresses referred to above. Support element 42A is advantageously a flexible metal bar or rod. In an alternative, instead of being connected to the web or sheet 41A it may be directly mated with the cooling tube(s). The connection may be by welding, adhesive, or, as shown in the figure, by a hinge 40A. While support element 42A is advantageously connected to the wall of vessel 20 at the point furthest laterally from its connecting point to the draft tube 16 (FIG. 2), it may be connected, instead or additionally) to another point on vessel 20. As shown in FIG. 5, three support elements (one shown by the combination of features 40A, 41A, 42A, the other equivalent elements not numbered for ease of view) are used, but more or less (or no) support elements may be used. Gaps in the circular array of plural cooling tubes 19A, 19B, etc. are shown in the figure to allow for support element shown individually by 42A. The riser column 15 and downcomer column 18 in the figure are the same as shown in the other figures. Such gaps in the array of cooling tubes 19A, 19B, etc. may be provided advantageously at the very bottom of the array simply by having the appropriate one or more cooling tubes shortened slightly.

Numerous modifications in the reactor according to the invention may be envisioned by one of ordinary skill in the art in possession of the present disclosure. For instance, as described above, the downcomer 18 is fitted with a hemispherical cap, 11 in FIG. 2, in order to eliminate a dead zone observed in a cold flow unit which had a flat head. However, a different geometry may be optimal under other conditions.

In another embodiment, a circular baffle just above the top of the riser may help spread the plume of gas outward and avoid any possible mass transfer limitations in the top of the reactor.

In yet another embodiment, there is a conical slope for the underside of the top head 10 in FIG. 2 (or FIG. 3) to facilitate the flow of the gas rich layer and/or avoid stagnant bubbles under the head to the central outlet hole 30.

In still another embodiment, reactor 8 (by reference to FIG. 2) may have a second cooling means provided around vessel 20, such as shown by element 3 in prior art FIG. 1.

Figure 6:
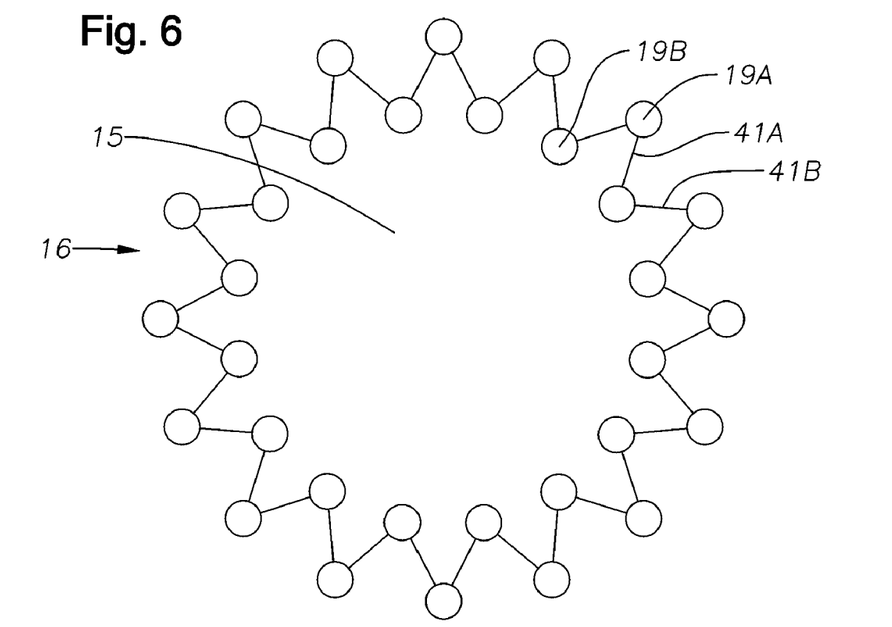
FIG. 6 shows a bottom view of the arrangement of cooling tubes according to an embodiment of the invention.

It will be appreciated that in the case of plural cooling tubes the pattern formed by the cooling tubes may be other than as illustrated in FIGS. 4A, 4B, and 5, i.e., other than in a circular pattern. It may be in an irregular pattern, or some other regular pattern, such as a square, rectangle, triangle, star pattern, and so on. FIG. 6 illustrates yet another alternative view of a cross-section of FIG. 2B across perspective line 4B, wherein plural cooling tubes 19A, 19B, etc., form a "zig-zag" pattern, connected by plural plates or webs illustrated by the single plate 41, to form the draft tube 16 separating riser column 15 and downcomer column 18. FIG. 6 can be seen to be one of many alternatives to the pattern shown by FIG. 4B.

In a preferred embodiment concerning construction and fabrication of the reactor according to the present invention, each individual cooling tube may be extruded with one or more fins along the outer wall, which may be used to weld the individual cooling tubes into the draft tube so as to provide the connective web or sheets represented by numerals 41A, 41B, etc.

It will be recognized by one of ordinary skill in the art in possession of the present invention that in a preferred embodiment wherein the draft tube comprises plural cooling tubes, a key mechanical feature of the present invention is that the conventional draft tube can be formed as an integral heat exchanger by welding individual heat exchanger tubes together into a shape, such as a circle, which divides the riser and downcomer columns. Without wishing to be bound by theory, among the benefits provided by this approach are that by welding the integral fins from each cooling tube together, the welded assembly assumes a significant stiffness much greater than any individual cooling tube. This stiffness allows the structure to withstand significant buckling stresses which may arise in certain reactions, such as found in the Oxo Reaction, as discussed elsewhere herein. It is preferred that lateral supports such as provided by the bar or rod indicated by 42A in FIG. 5 be kept to a minimum, as such supports may detrimentally affect process pressure drop and provide locations for the deposition of material (such as cobalt catalyst in the case of the conventional Oxo Reaction).

The reactor according to the present invention is particularly suitable for carrying out an exothermic gas-liquid chemical reaction. The reactor may be provided in series or in parallel with other reactors of the same type (e.g., internal loop reactors according to the invention or according to the prior art) or different types, such as one or more external loop reactors in series with one or more reactors according to the present invention. In the case where the reaction is endothermic the heat exchange medium is selected to be suitable for providing heat to the reaction medium, which is within the skill of the ordinary artisan.

In a preferred embodiment, the reactor according to the present invention will be downstream of the main Oxo Reactors. In still more preferred embodiments, up to about 10 to 15% of the overall Oxo reaction may occur in the reactor according to the present invention when arrayed in series with plural additional external and/or internal loop reactors. Other configurations are possible, such as providing a reactor according to the present invention in a reactor array such as described in U.S. Pat. No. 5,763,678. However, it is to be understood that the reactor according to the present invention may function as a stand-alone reactor providing 100% of the reaction product in a continuous or batch reaction.

Thus, in embodiments, the invention also relates to a process for catalytic hydroformylation of an olefin feedstock by syn gas comprising feeding a stream comprising olefin and/or the product of a hydroformylation reaction having said olefin as a starting material, said stream comprising syn gas, to the inlet of a reactor and obtaining as a product of said reactor a stream comprising syn gas and said product of a hydroformylation reaction, the improvement comprising an internal loop reactor characterized by a plurality of cooling tubes forming the annulus between the riser and the downcomer path of said internal loop reactor. The reaction is also characterized by its very large volume, such as at least 15 cubic meters, or at least 20 cubic meters, or at least 25 cubic meters, or more preferable at least 30 cubic meters.

In a preferred embodiment, in place of or in addition to thermocouples placed at various points in the reactor, such as at elements 22A, 22B, 22C, 22D, in FIG. 2A, it may be advantageous to use an analog continuous signal from a standard flow switch (for example as supplied by numerous vendors such as Fluid Components International) to give a continuous trend readout of the circulation velocity. In a preferred embodiment, such a switch would be adapted to be inserted into one of the aforementioned thermocouple nozzles.

In another preferred embodiment, flush mounting of the outlet nozzle to the inside of the head to avoid gas pockets which could allow the onset of Fischer Tropsch reactions.

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

What is claimed is:

1. An apparatus for contacting two reactants to produce at least one product, said apparatus comprising:
   a vertically disposed vessel having a vertical axis, a sidewall, an upper portion and a lower portion;
   a draft tube comprising at least one heat exchange means, said draft tube providing a riser conduit within said draft tube and a downcomer conduit between said draft tube and said sidewall, said draft tube extending into the upper portion of said vessel and comprising at least one opening in said upper portion so as to provide fluid flow communication between the riser conduit and the downcomer conduit and extending into the lower portion of said vessel and comprising at least one opening in said lower portion so as to provide fluid flow communication between the riser conduit and the downcomer conduit;
   an inlet means for introducing said reactants; and
   a gas outlet;
   wherein said draft tube is demountable engaged with said vessel sidewall in said lower portion of said vessel.

2. The apparatus according to claim 1, wherein said upper portion of said vessel comprises a vessel head comprising said gas outlet means, wherein said draft tube is suspended from said vessel head.

3. The apparatus according to claim 2, wherein said vessel head is demountably engaged with said vessel sidewall.

4. The apparatus according to claim 1, wherein the volume of said vessel is at least 20 cubic meters.

5. A process for carrying out a reaction to form a product in the apparatus according to claim 1, which comprises:
   introducing at least one liquid reactant and at least one gaseous reactant through said inlet means so that said at least one liquid reactant and at least one gaseous reactant travel generally upward in said riser conduit of said draft tube comprising at least one heat exchange means and reacting said at least one liquid reactant and said at least one gaseous reactant to form said at least one product while said reacting produces or consumes heat, said heat being exchanged with said heat exchange means;
   passing at least one gas out of said apparatus through said gas outlet;
   passing a fluid comprising said at least one liquid reactant and/or said at least one product through said at least one opening in said upper portion and then in a generally downward direction in said downcomer conduit;
   and isolating said product.

6. The process of claim 5, wherein said heat exchange means comprises at least one cooling tube.

7. The process of claim 5, wherein said heat exchange means comprises a plurality of cooling tubes.

8. The process of claim 5, wherein said reaction is the Oxo Reaction.

9. In a process for catalytic hydroformylation of an olefin feedstock by syn gas comprising feeding a stream comprising olefin and/or the product of a hydroformylation reaction having said olefin as a starting material, said stream comprising syn gas, to the inlet of an internal loop reactor according to claim 1 and obtaining as a product of said reactor a stream comprising syn gas and said product of a hydroformylation reaction, the improvement comprising a heat exchanger forming the draft tube between the riser column and the downcomer column of said internal loop reactor.

10. The process of claim 9, wherein the volume of said internal loop reactor is at least 20 cubic meters.

11. The process of claim 9, wherein said heat exchanger comprises a plurality of cooling tubes.

12. An internal loop reactor according to claim 1 characterized by a plurality of cooling tubes forming a draft tube between a riser column and a downcomer column of said internal loop reactor.

13. The reactor of claim 12, wherein said reactor is further characterized by a removable top capping said reactor, and wherein the plurality of cooling tubes are attached to said top.

14. The reactor of claim 12, wherein at least a portion of the bottom of said draft tube comprising a plurality of cooling tubes is attached to the wall of said internal loop reactor.

* * * * *